(12) United States Patent
Rouet et al.

(10) Patent No.: US 11,069,059 B2
(45) Date of Patent: Jul. 20, 2021

(54) PRENATAL ULTRASOUND IMAGING

(71) Applicant: KONINKLIJKE PHILIPS N.V., Eindhoven (NL)

(72) Inventors: Jean-Michel Rouet, Paris (FR); Matthieu Perrot, Suresnes (FR); Cybèle Ciofolo-Veit, Meudon (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 16/470,213

(22) PCT Filed: Dec. 14, 2017

(86) PCT No.: PCT/EP2017/082901
§ 371 (c)(1),
(2) Date: Jun. 15, 2019

(87) PCT Pub. No.: WO2018/109114
PCT Pub. Date: Jun. 21, 2018

(65) Prior Publication Data
US 2020/0090327 A1    Mar. 19, 2020

(30) Foreign Application Priority Data
Dec. 15, 2016   (EP) .................................... 16306690

(51) Int. Cl.
*G06T 7/00*     (2017.01)
*G06T 7/11*     (2017.01)
(Continued)

(52) U.S. Cl.
CPC .......... *G06T 7/0012* (2013.01); *A61B 8/0866* (2013.01); *A61B 8/4245* (2013.01);
(Continued)

(58) Field of Classification Search
CPC ......... G06T 7/0012; G06T 7/11; G06T 7/337; G06T 2207/10132; G06T 2207/20104;
(Continued)

(56) References Cited

U.S. PATENT DOCUMENTS 5,588,435 A    12/1996 Weng et al.
5,605,155 A    2/1997 Chalana et al.
(Continued)

FOREIGN PATENT DOCUMENTS

IN    5859CH2013 A    6/2015
JP    2009261800 A    11/2009
(Continued)

OTHER PUBLICATIONS

International Search Report and Written Opinion for International Application Serial No. PCT/EP2017/082901, filed Dec. 14, 2017, 17 pages.
(Continued)

*Primary Examiner* — Nimesh Patel

(57) ABSTRACT

An ultrasound system (100) and operating method (200) are disclosed in which the system is adapted to receive a sequence (15) of 2-D ultrasound image frames (150) of a prenatal entity from an ultrasound probe (14) and, for each image frame in said sequence, control the display device to display the received image frame; attempt to segment the image frame for recognition of an anatomical feature of interest (151) of said prenatal entity in said image frame; and accept the image frame for further processing upon recognition of said feature, said further processing comprising: determine a geometric property of the recognized anatomical feature of interest for each accepted image frame; and control the display device to display the determined geometric properties of the accepted image frames in said sequence with each displayed image frame. Such an oper-
(Continued)

ating method may be made available as a computer program product for installation on the ultrasound system.

11 Claims, 7 Drawing Sheets

(51) Int. Cl.
  *G06T 7/33* (2017.01)
  *A61B 8/08* (2006.01)
  *A61B 8/00* (2006.01)
(52) U.S. Cl.
  CPC ............... *G06T 7/11* (2017.01); *G06T 7/337* (2017.01); *G06T 2207/10132* (2013.01); *G06T 2207/20104* (2013.01)
(58) Field of Classification Search
  CPC ..... G06T 2210/41; G06T 19/00; G06T 17/00; G06T 2200/04; G06T 2207/30004; G06T 2207/30241; G06T 15/08; G06T 2207/10072; G06T 11/008; G06T 2207/30008; G06T 7/0014; G06T 7/246; G06T 7/55; G06T 2207/20044; G06T 2207/20072; G06T 2207/30168; G06T 3/0068; G06T 7/136; G06T 7/62; G06T 7/30; G06T 7/187; G06T 2200/08; G06T 2207/10136; G06T 2219/2004; G06T 2219/2021; G06T 2207/20081; A61B 8/0866; A61B 8/4245; A61B 8/463; A61B 8/5223; A61B 8/145; A61B 8/483; A61B 8/488; A61B 8/06; A61B 8/466; G16H 50/30; G06K 9/00671; G06K 2009/00738; G06K 9/00711; G06K 2209/05; G06K 9/00771; G06K 2209/057; G06K 9/00765; G06K 9/00597; G06K 9/0061; G06K 9/342; G06K 9/4604; G06K 9/4642; G06K 9/6212; G06K 2009/484; G06K 2209/055; G06K 9/2063; G06K 9/48; G06K 9/00255; G06K 9/00201; G06K 9/00342; G06K 9/4671; G06K 9/6218; G06K 9/32; G06K 9/34; G06K 9/6267; G06N 20/00; G06N 3/08; G06N 3/0454; G06N 3/084; G06N 5/003; G06N 5/046
  See application file for complete search history.

(56) References Cited

U.S. PATENT DOCUMENTS

| | | | |
|---|---|---|---|
| 8,891,881 B2 | 11/2014 | Gupta et al. | |
| 2002/0072671 A1* | 6/2002 | Chenal | A61B 8/485 600/450 |
| 2006/0058651 A1 | 3/2006 | Chiao et al. | |
| 2007/0081705 A1 | 4/2007 | Carneiro et al. | |
| 2012/0016237 A1 | 1/2012 | Tanigawa | |
| 2012/0016238 A1 | 1/2012 | Matsumara | |
| 2012/0071758 A1* | 3/2012 | Lachaine | A61N 5/1049 600/439 |
| 2012/0078101 A1 | 3/2012 | Kim et al. | |
| 2012/0162375 A1 | 6/2012 | Vlutters et al. | |
| 2012/0176365 A1* | 7/2012 | Hansegard | A61B 8/469 345/419 |
| 2013/0137983 A1 | 5/2013 | Shin et al. | |
| 2014/0148696 A1 | 5/2014 | Yoo et al. | |
| 2014/0185895 A1 | 7/2014 | Swamy et al. | |
| 2014/0358000 A1 | 12/2014 | Gupta et al. | |
| 2015/0086093 A1 | 3/2015 | Fonte et al. | |
| 2015/0327841 A1* | 11/2015 | Banjanin | A61B 8/5276 600/443 |
| 2016/0045152 A1 | 2/2016 | Singhal et al. | |
| 2016/0063758 A1* | 3/2016 | Schroecker | G06F 16/51 345/426 |
| 2016/0081663 A1* | 3/2016 | Chen | A61B 8/0866 600/425 |
| 2016/0324584 A1* | 11/2016 | Tahmasebi Maraghoosh | A61B 34/20 |

FOREIGN PATENT DOCUMENTS

| | | |
|---|---|---|
| WO | 2016001784 A1 | 1/2016 |
| WO | 201638491 A1 | 3/2016 |

OTHER PUBLICATIONS

Shrimali, et al., "Improved Segmentation of Ultrasound Images for Fetal Biometry Using Morphological Operators", 31st Annual International Conference of the IEEE EMBS, Minneapolis, Minnesota, USA, Sep. 2-6, 2009, pp. 459-462.
Yu, et al., "Fetal Abdominal Contour Extraction and Measurement in Ultrasound Images", Ultrasound in Medicine and Biology, vol. 34, No. 2, pp. 169-182.
Salomon, et al., "Practice guidelines for performance of the routine mid-trimester fetal ultrasound scan", Ultrasound Obstet Gynecol 2011; 37: pp. 116-126.
Hanna, et al., "Automated Measurements in Obstetric Ultrasound Images", International Conference on Image Processing, Oct. 26-29, 1997, vol. 3, pp. 504-507.
Thomas, et al, "Automatic Segmentation of Ultrasound Images Using Morphological Operators", IEEE Transactions on Medical Imaging, vol. 10, No. 2, Jun. 1991, pp. 180-186.
Peters, et al., "Automatic segmentation of ultrasound images using morphological operators," in Medical Imaging, IEEE Transactions on , vol. 10, No. 2, Jun. 1992, pp. 180-186. (Abstract).

* cited by examiner

PRENATAL ULTRASOUND IMAGING

RELATED APPLICATIONS

This application is the U.S. National Phase application under 35 U.S.C. § 371 of International Application No. PCT/EP2017/082901, filed on Dec. 14, 2017, which claims the benefit of European Application No. 16306690.5, filed Dec. 15, 2016. These applications are hereby incorporated by reference herein.

FIELD OF THE INVENTION

The present invention relates to an ultrasound system comprising a processor arrangement and a display device under control of the processor arrangement, wherein the processor arrangement is adapted to receive a sequence of 2-D ultrasound image frames of a prenatal entity from an ultrasound probe and to control the display device to display the received image frames.

The present invention further relates to a method of operating such an ultrasound system.

The present invention further relates to a computer program product comprising a computer readable storage medium having computer readable program instructions embodied therewith for, when executed on the processor arrangement of such an ultrasound system, cause the processor arrangement to implement such a method.

BACKGROUND OF THE INVENTION

Ultrasonic imaging is routinely used during pregnancy to assess the development of a prenatal entity, typically a fetus, in the mother's womb, for example to detect structural anomalies in the fetus. The traditional way for a clinician to acquire an image of each required view of the prenatal entity is to manipulate an ultrasound probe while in acoustic contact with the abdomen of the mother until a desired anatomical orientation is in the plane of the 2D imaging probe. If multiple views are to be generated with such a procedure, for example to image an anatomical feature of interest of the prenatal entity in its entirety, the sonographer may move the ultrasound probe over the abdomen of the mother in a particular direction to obtain a temporal sequence of 2D image frames.

This for example may be of interest to analyse the development of the prenatal entity, e.g. fetus, using so-called biometry measurements, which are used to check if one or more anatomical features of interest of the prenatal entity are developing correctly, e.g. within expected tolerances, and/or to estimate gestational age. This may require the sonographer to evaluate each captured image frame in order to perform these measurements, which can be time-consuming. Moreover, if the image frame sequence is obtained by movement of the ultrasound probe in a non-optimal direction along the mother's abdomen, several of the image frames may include the anatomical feature of interest in a distorted manner or may not include the anatomical feature of interest at all. This can make the acquisition of such biometric measurements rather cumbersome and time-consuming.

It is well-known that various fetal anatomical features of interest may be extracted from a 2D ultrasound image frame using so-called image segmentation techniques in which an outline of the anatomical features of interest is identified as a segment of the image frame, after which the biometric evaluation of the identified feature may be (automatically) performed. For example, Jinhua Yu et al. in Ultrasound in Med. & Biol. Vol. 34, No. 2, pp 169-182 (2008) disclose a method for fetal abdominal contour extraction and measurement from 2D ultrasound image frames, whilst Judith G. Thomas et al. in IEEE Transactions on Medical Imaging, Vol. 10, No. 2 (1991), pages 180-186 disclose the automatic segmentation of ultrasound images using morphological operators, to name but a few examples of such well-known algorithms.

U.S. Pat. No. 8,891,881 B2 discloses a method for identifying an optimal image frame. The method includes receiving a selection of an anatomical region of interest in an object of interest. Furthermore, the method includes obtaining a plurality of image frames corresponding to the selected anatomical region of interest. The method also includes determining a real-time indicator corresponding to the plurality of acquired image frames, wherein the real-time indicator is representative of quality of an image frame. In addition, the method includes communicating the real-time indicator to aid in selecting an optimal image frame. This method therefore may be used to identify the most promising image frame for biometric evaluation. However, this method does not aid the sonographer in identifying a suitable direction for ultrasound probe movement in order to generate a sufficient number of 2D image frames in which a fetal anatomical feature of interest can be reliably recognized.

US 2014/0185895 A1 discloses a computer-implemented method for analyzing a fetal ultrasound image that includes accessing a first statistical model calculated from training data representing shapes of conforming fetal abdominal tissue exemplars and accessing image data representing a scan plane in an ultrasound image. The method further includes identifying a region of interest including an abdomen in the scan plane using the first statistical model, accessing a second statistical model calculated from training data representing shapes of conforming fetal anatomical structure exemplars, determining whether one or more anatomical structures are present within the region of interest using the second statistical model, and assigning a rating to the scan plane based on the presence of the one or more anatomical structures in the region of interest.

US 2007/0081705 A1 discloses a method for segmenting and measuring anatomical structures in fetal ultrasound images that includes the steps of providing a digitized ultrasound image of a fetus comprising a plurality of intensities corresponding to a domain of points on a 3-dimensional grid, providing a plurality of classifiers trained to detect anatomical structures in said image of said fetus, and segmenting and measuring an anatomical structure using said image classifiers by applying said elliptical contour classifiers to said fetal ultrasound image, wherein a plurality of 2-dimensional contours characterizing said anatomical structure are detected.

US 2016/0045152 A1 discloses a method for automatically monitoring fetal head descent in a birth canal including segmenting each image in one or more images into a plurality of neighborhood components, determining a cost function corresponding to each neighborhood component in the plurality of neighborhood components in each of the one or more images, identifying at least two structures of interest in each image in the one or more images based on the cost function, wherein the at least two structures of interest include a pubic ramus and a fetal head, measuring an angle of progression based on the at least two structures of interest, and determining the fetal head descent in the birth canal based on the angle of progression.

SUMMARY OF THE INVENTION

The present invention seeks to provide an ultrasound system that can assist a sonographer in guiding an ultrasound probe in a suitable direction over a mother's abdominal area to obtain a useful sequence of 2D images of the prenatal entity.

The present invention further seeks to provide a method of operating such an ultrasound system.

The present invention still further seeks to provide a computer program product comprising a computer readable storage medium having computer readable program instructions embodied therewith for, when executed on the processor arrangement of such an ultrasound system, cause the processor arrangement to implement such a method.

According to an aspect, there is provided an ultrasound system comprising a processor arrangement and a display device under control of the processor arrangement, wherein the processor arrangement is adapted to receive a sequence of 2-D ultrasound image frames of a prenatal entity from an ultrasound probe, said sequence defining a sliding window of 2-D ultrasound image frames along a translation direction, and, for each image frame in said sequence, control the display device to display the received image frame; attempt to segment the image frame for recognition of an anatomical feature of interest of said prenatal entity in said image frame; and accept the image frame for further processing upon recognition of said feature, said further processing comprising determine a geometric property of the recognized anatomical feature of interest for each accepted image frame; and control the display device to display the determined geometric properties of the accepted image frames in said sequence with each displayed image frame.

In accordance with embodiments of the present invention, the ultrasound system evaluates the respective image frames that it receives from the ultrasound probe and attempts to segment the image frames in order to isolate (recognize) an anatomical feature of interest in the image frames, typically using a suitable segmentation algorithm. The anatomical feature of interest for example may be selected by a user such as a sonographer of the ultrasound system, e.g. using a user interface or the like. For those image frames for which the segmentation is considered successful by the system, the system keeps track of the geometric properties of the various accepted image frames and displays these geometric properties together with each displayed image frame of the sequence, such that for each image frame that is displayed the sonographer is provided with an indication of a spread or variance of the obtained geometric properties in the respective image frames of the sequence, thereby providing the sonographer with a clear indication of the suitability of the direction in which a sonographer moves the ultrasound probe across a region of interest such as an abdominal region of the mother of the prenatal entity such as a fetus. Consequently, the sonographer is provided with real-time feedback about the suitability of the path across which the ultrasound probe is moved by the sonographer, such that the sonographer may alter this path if this feedback is indicative of a sub-optimal path.

Determination of the geometric property may comprise determination of a dimension of the recognized anatomical feature such as a diameter or circumference of the fetal head or abdomen, femur length, nuchal translucency, by-parietal diameter, and so on. Any anatomical feature for which an automatic detection and segmentation algorithm is available may be contemplated.

In a preferred embodiment, the processor arrangement is adapted to calculate a deviation of the determined geometric property from a reference value and to control the display device to display each determined geometric property in a manner indicative of a result of said calculation. In this manner, a user such as a sonographer gets immediate visual feedback about the reliability of the determined geometric property. For example, in case of an unreliable or potentially spurious property value, the value may be displayed in red whereas in case of a reliable property value, this value may be displayed in green such that the user can immediately recognize the relevance of a determined geometric property of an anatomical feature of interest as identified in the segmented image frame.

The processor arrangement may be adapted to control the display device to display the determined geometric properties of the accepted images in said sequence in any suitable manner, such as a graph. A graph representation has the advantage that the variance of the determined geometric property of time can be recognized in a straightforward manner by the user.

In an embodiment, the processor arrangement is adapted to control the display device to display an overlay over the recognized anatomical feature including the determined geometric property if the displayed image frame is an accepted image frame such that the user is presented in real-time with the determined geometric property when the accepted image frame corresponding to the determined geometric property is displayed on the display device. This for example may include displaying the overlay in a manner that is indicative of the aforementioned calculation of the deviation of the determined geometric property from the reference value such that the user can readily distinguish between reliable values and potentially spurious values.

Preferably, the processor arrangement is further adapted to assess whether the sequence of images frames as a whole is acceptable. To this end, the processor arrangement may be adapted to determine a variation in the determined geometric property across the plurality of accepted image frames; reject the plurality of accepted image frames if the determined variation exceeds a defined threshold; and control the display device to display an indication of said rejection. This provides the user with feedback information that a particular sequence of image frames is particularly noisy, such that the user is encouraged to recapture the sequence of image frames by moving the ultrasound probe in a different direction across the region of interest, the choice of which direction may be based on captured image frames for which a reliable geometric property of the anatomical feature of interest could be determined.

The processor arrangement may be arranged to make this rejection of the plurality of accepted image frames if the determined variation exceeds the defined threshold; and a ratio of a total number of accepted image frames in a complete sequence of image frames and a total number of image frames in the complete sequence of image frames is below a defined further threshold.

In a preferred embodiment, the ultrasound system further comprises a data storage arrangement, wherein the processor arrangement is adapted to store the accepted image frames and the determined geometric properties in the data storage arrangement for evaluation of the image frames and/or the determined geometric properties at a later point in time, e.g. at any suitable point in time by simple retrieval of the images from the data storage arrangement, e.g. a memory, for example by means of a user interface for selecting one or more images from the sequence.

The ultrasound system does not necessarily include the ultrasound probe, as the ultrasound probe may be external to the ultrasound system, for example when the ultrasound system comprises implements an ultrasound diagnosis apparatus to which the ultrasound probe may be attached. Alternatively, the ultrasound system further comprises the ultrasound probe, e.g. may form a complete ultrasound imaging system.

In the above embodiments, the sequence of image frames may be a sequence of 2-D image frames captured by the sonographer moving the ultrasound probe over a region of interest as previously explained. However, embodiments of the present invention may be usefully applied to a 3-D image, i.e. a volumetric image, wherein the sequence of image frames form part of this volumetric image. In particular, the ultrasound system may respond to a user command for slicing the volumetric image in a particular direction, thereby generating a plurality of 2-D image slices (frames) for which the ultrasound system may attempt to segment each slice and derive a geometric property of anatomical feature of interest for successfully segmented slices, and maintain a history of the derived geometric properties, which history may provide an indication of the suitability of the chosen slicing direction in the assessment of a particular anatomical feature of interest, such that the user of the system may use this feedback to choose a different slicing direction in order to obtain the optimal view of the anatomical feature of interest in the 2-D image slices resulting from the chosen slicing direction.

According to another aspect, there is provided a method for operating an ultrasound system comprising a processor arrangement and a display device under control of the processor arrangement, the method comprising, with the processor arrangement, receiving a sequence of 2-D ultrasound image frames of a prenatal entity from an ultrasound probe, said sequence defining a sliding window of 2-D ultrasound image frames along a translation direction, and for each image frame in said sequence, controlling the display device to display the received image frame; attempting to segment the image frame for recognition of an anatomical feature of interest of said prenatal entity in said image frame; and accepting the image frame for further processing upon recognition of said feature, said further processing comprising determining a geometric property of the recognized anatomical feature of interest for each accepted image frame; and controlling the display device to display the determined geometric properties of the accepted images in said sequence with each displayed image frame. In this manner, a user of the ultrasound system pertains real-time feedback information regarding the stability of the geometric property across the sequence of image frames, which feedback information may be used by the user to readjust the direction in which the ultrasound probe is moved across the region of interest such as an abdominal region of a mother carrying a prenatal entity in order to improve the suitability of the sequence of image frames for determining the geometric property of the anatomical feature of interest of this prenatal entity.

This may include calculating a deviation of the determined geometric property from a reference value and to control the display device to display each determined geometric property in a manner indicative of a result of said calculation to more clearly highlight to the user whether a determined geometric property can be relied on.

In an embodiment, the method further comprises controlling the display device to display an overlay over the recognized anatomical feature including the determined geometric property if the displayed image frame is an accepted image frame such that the user gets a real-time indication of the geometric property, which indication may be used by the user to readjust the direction in which the ultrasound probe is moved across the region of interest.

In addition, the method may further comprise determining a variation in the determined geometric property between the plurality of accepted image frames; rejecting the plurality of accepted image frames if the determined variation exceeds a defined threshold; and controlling the display device to display an indication of said rejection to aid the user in determining if the acquired sequence is of sufficient quality for evaluating the geometric property of interest of the prenatal entity such as a fetus.

According to yet another aspect, there is provided a computer program product comprising a computer readable storage medium having computer readable program instructions embodied therewith for, when executed on a processor arrangement of an ultrasound system according to any embodiment of the present invention, cause the processor arrangement to implement the method according to any embodiment of the present invention. Such a computer program product may be used to augment or otherwise configure the functionality of ultrasound system, e.g. by installing the computer readable program instructions on the system.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
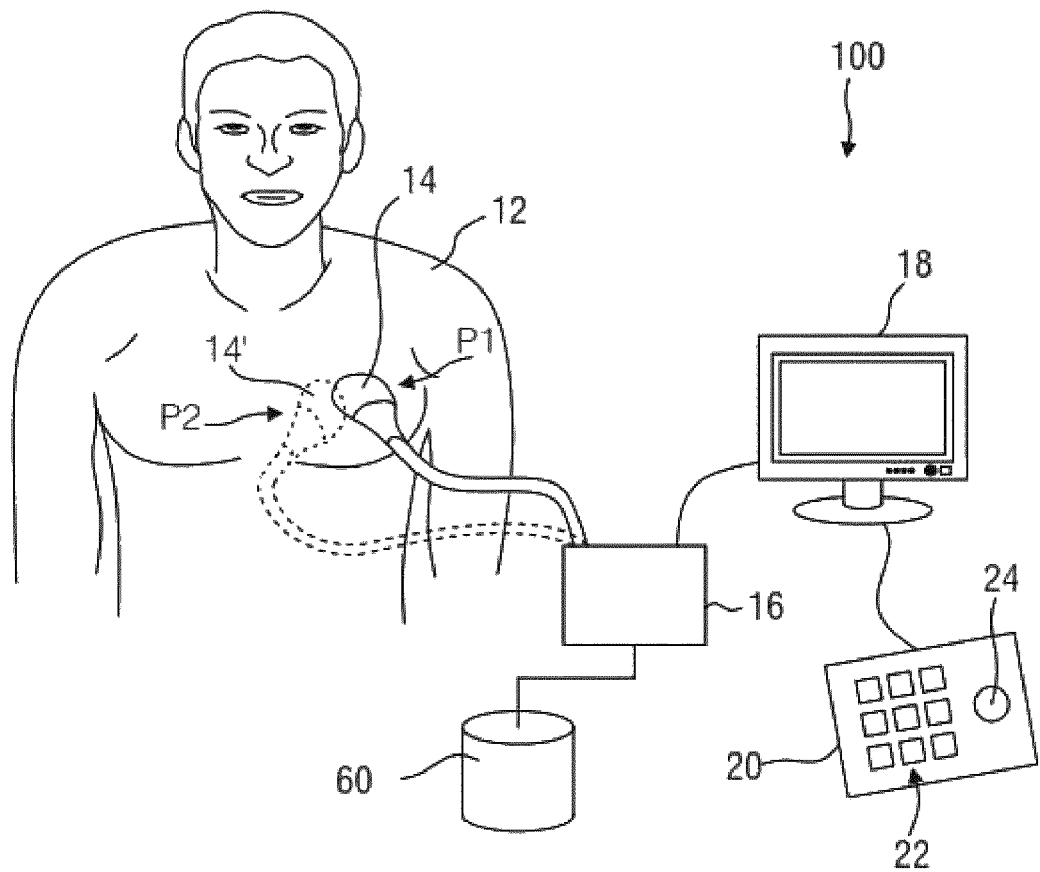
FIG. 1 shows a schematic representation of an ultrasound imaging system in use to scan a part of a patient's body.

It should be understood that the Figures are merely schematic and are not drawn to scale. It should also be understood that the same reference numerals are used throughout the Figures to indicate the same or similar parts.

FIG. 1 shows a schematic illustration of an ultrasound system 100, in particular a medical two-dimensional (2D) ultrasound imaging system or three-dimensional (3D) ultrasound imaging system. The ultrasound system 100 may be applied to inspect a volume of an anatomical site, in particular an anatomical site of a patient 12 over time. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements may be arranged in a linear array in case of a 2D ultrasound system 100 or may be arranged in a two-dimensional array, in particular for providing a multi-planar or three-dimensional image in case of a 2D ultrasound system 100.

A particular example for a three-dimensional ultrasound system which may be the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

Further, the ultrasound system 100 may comprise a processor arrangement including an image reconstruction unit 16 that controls the provision of a 2D or 3D image sequence via the ultrasound system 100. As will be explained in further detail below, the image reconstruction unit 16 may control not only the acquisition of data via the transducer array of the ultrasound probe 14, but also signal and image processing that form the 2D or 3D image sequence out of the echoes of the ultrasound beams received by the transducer array of the ultrasound probe 14.

The ultrasound system 100 may further comprise a display device 18 (from here on also referred to as display 18) for displaying the 2D or 3D image sequence to the user. Still further, an input device 20 may be provided that may comprise keys or a keyboard 22 and further inputting devices, for example a trackball 24. The input device 20 might be connected to the display 18 or directly to the image reconstruction unit 16.

The ultrasound system 100 may further comprise a data storage arrangement 60, e.g. one or more memory devices, hard disks, optical discs, or the like, in which the image reconstruction unit 16 may store image frames and image frame processing data, e.g. for evaluation at a later date, as will be explained in more detail below.

Figure 2:
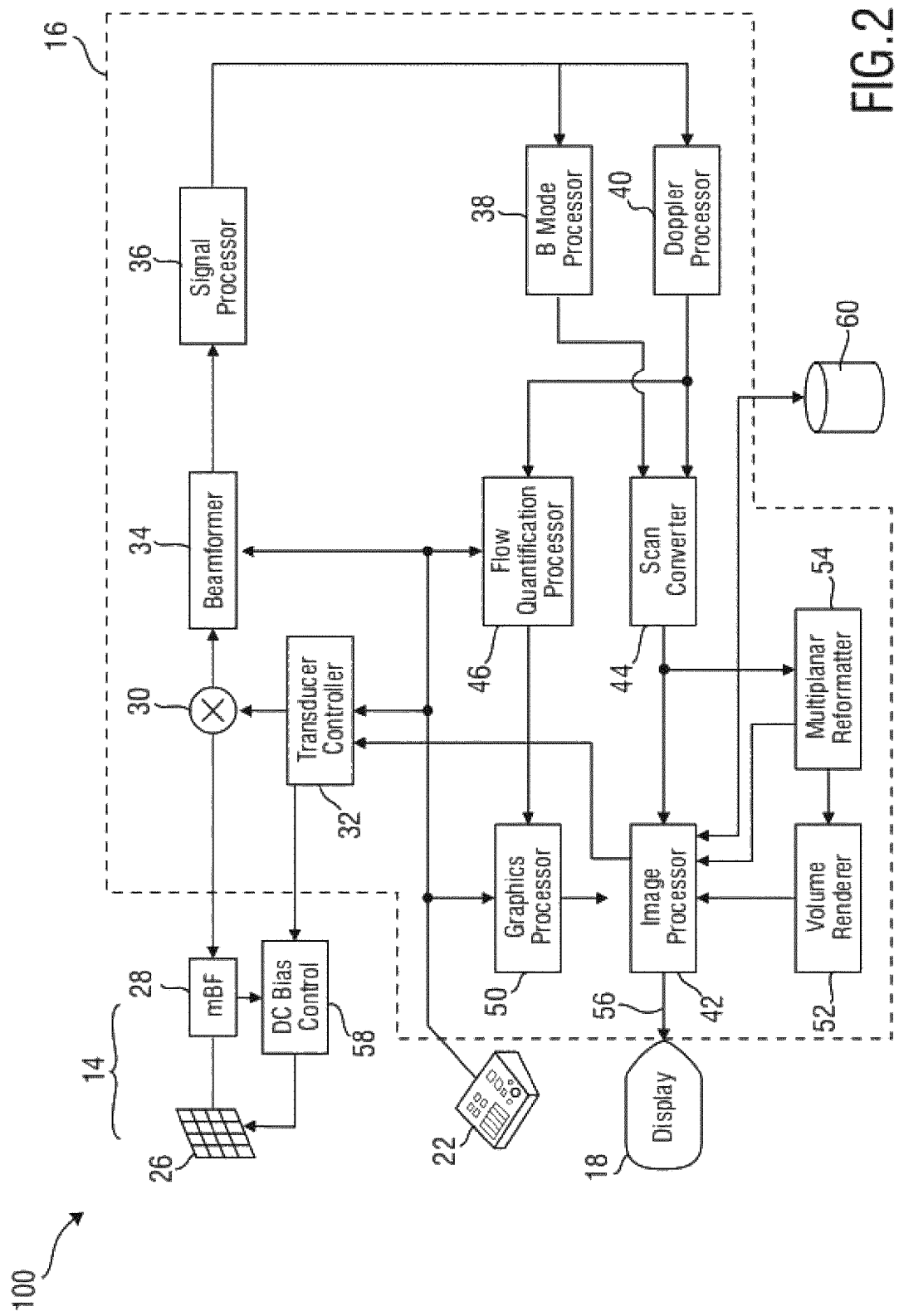
FIG. 2 shows a schematic block diagram of an embodiment of an ultrasound imaging system with an array transducer.

FIG. 2 illustrates a schematic block diagram of the ultrasound system 100. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in two dimensions for 2D imaging or in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field.

In a 3D imaging system, the multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18.

In addition to being used for imaging, the blood flow values produced by the Doppler processor 40 and tissue structure information produced by the B mode processor 38 may be transferred to a quantification processor 46 forming part of the processor arrangement. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 forming part of the processor arrangement for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like, as will be explained in more detail below. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images in case of a 3D imaging system.

Again, it shall be noted that the aforementioned ultrasound system 100 has only been explained as one possible example for an application of the medical ultrasound image processing device 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 2.

Figure 3:
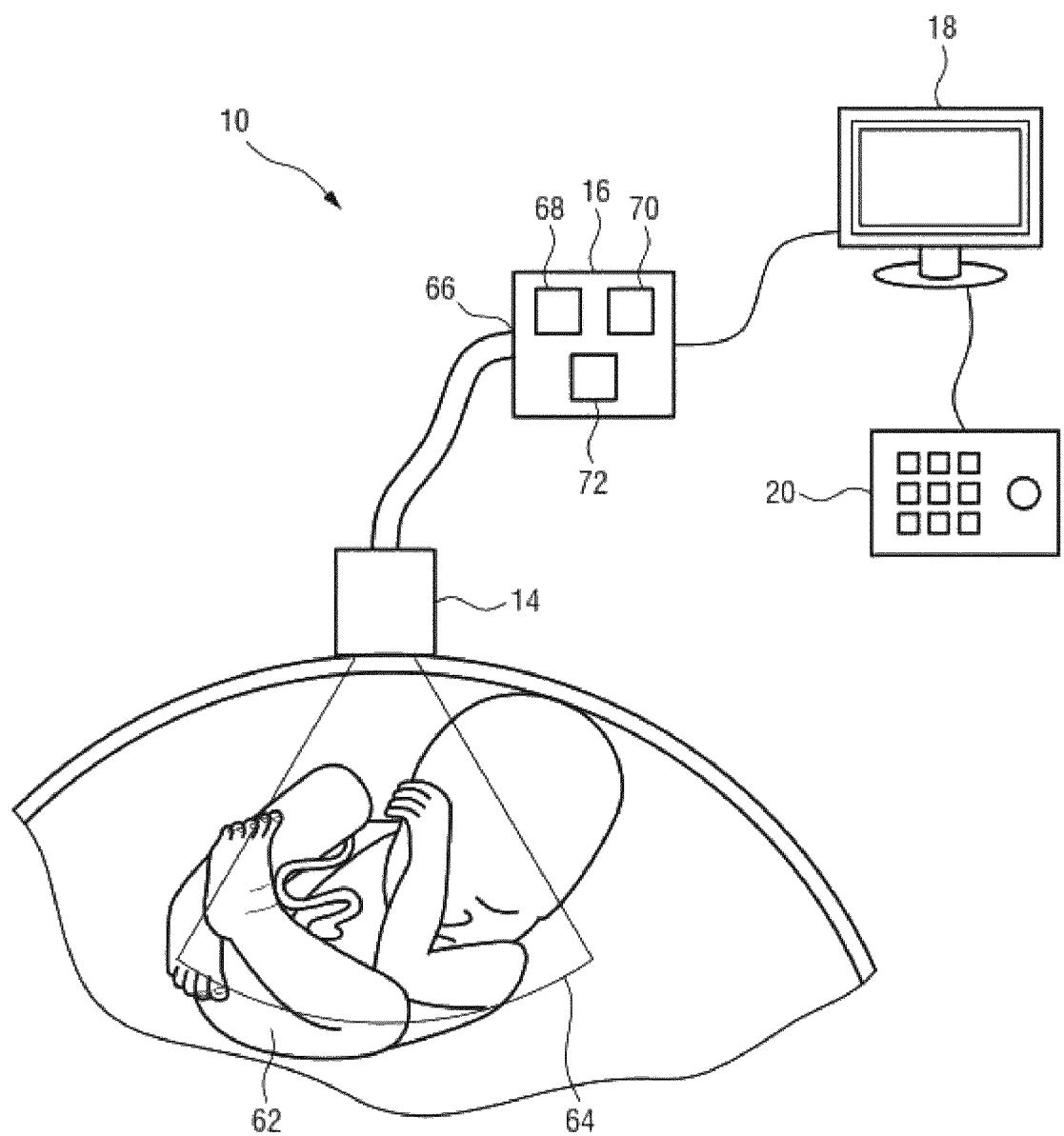
FIG. 3 shows a schematic diagram of the ultrasound imaging apparatus for scanning a fetus.

FIG. 3 shows a schematic view of the ultrasound diagnosis apparatus which is generally denoted by 10. The ultrasound diagnosis apparatus 10 scans by means of the ultrasound probe 14 a fetus, which is generally denoted by 62. The ultrasound probe 14 scans an anatomical site, which forms a region of interest and which is generally denoted by 64. The ultrasound probe 14 is connected to the image reconstruction unit 16 via an ultrasound data interface 66 and which comprises a segmentation unit 68, a measurement unit 70 and a calculation unit 72. The image reconstruction unit 16 is connected to the display 18 for displaying the results of the ultrasound scan and which is connected to the input device 20 for inputting instructions to control the medical ultrasound diagnosis apparatus 10.

The segmentation unit 68 is provided for segmenting anatomical structures of the fetus 62 in the 3D ultrasound data captured by the ultrasound probe 14 and the segmentation unit 68 provides segmentation data of the anatomical structures of the fetus 62. The measurement unit 72 is provided for measuring the anatomical structures of the fetus 62 based on the segmentation data provided by the segmentation unit 68. The calculation unit 72 is configured to calculate at least one biometric parameter of the fetus 62 based on the segmentation data provided by the segmentation unit 68. Based on the so-determined at least one biometric parameter, different biometric analyses can be performed, in particular the gestational age of the fetus 62 can be calculated based on measured sizes of anatomical structures in the head of the fetus 62.

Figure 4:
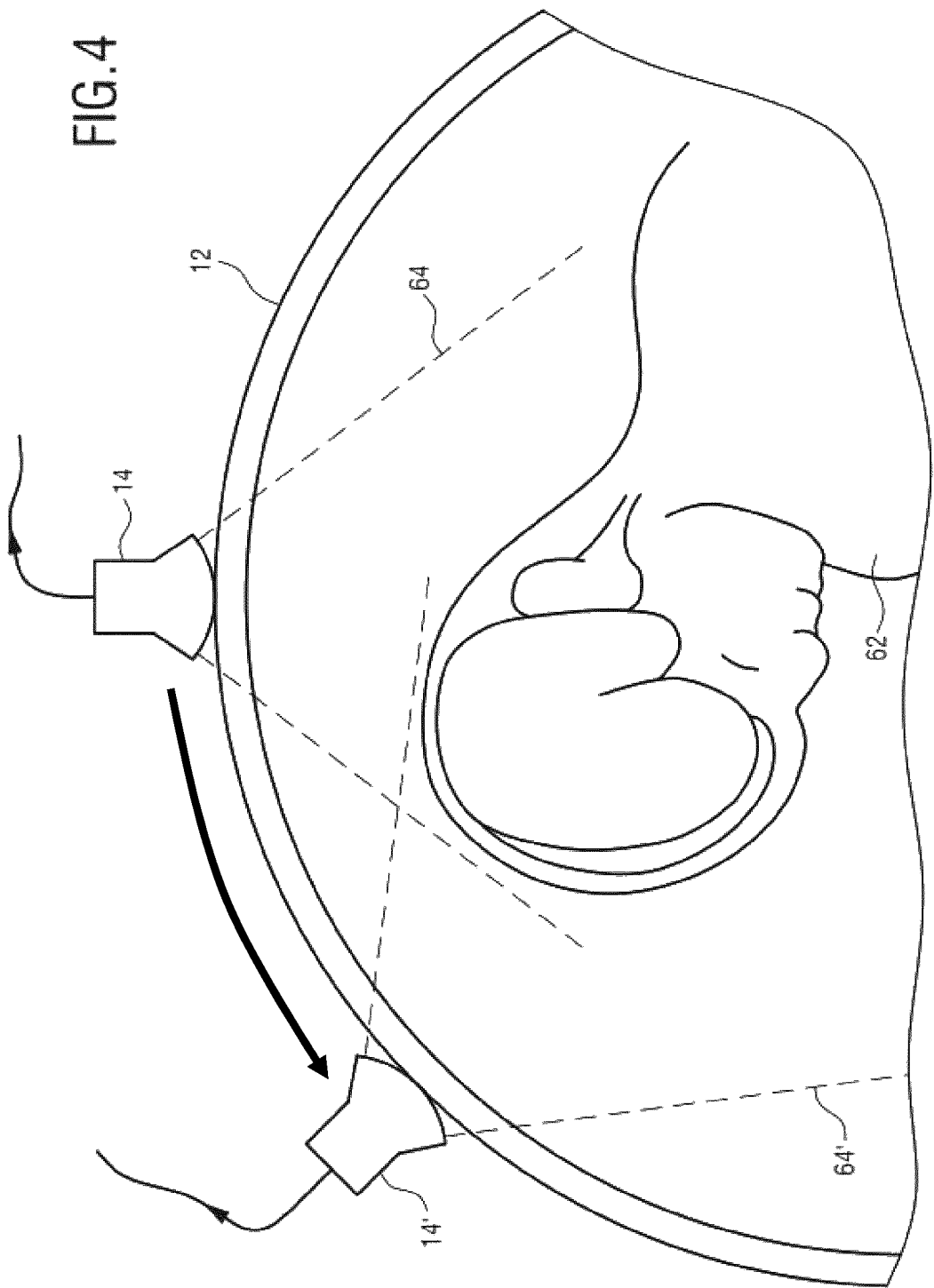
FIG. 4 shows a schematic diagram of the patient to be scanned in two different viewing directions.

FIG. 4 shows a detailed schematic diagram of the object 12 to be scanned by the ultrasound probe 14, wherein in this particular case the object is a fetus 62 to be scanned and to determine a gestational age based on biometric sizes of different individual biometrical parameter within the head of the fetus 62.

In order to measure the biometric parameter, at first a plurality of ultrasound scans are performed at different positions with different regions of interest 64, 64', as shown in FIG. 4 and the scans are provided via the ultrasound data interface 66 to the segmentation unit 68 in order to perform a model-based segmentation followed by a model-based measurement.

In the particular case shown in FIG. 4, a calculation of the gestational age is performed on all different individual biometric measurements, wherein a direct trust correlation of the individual measurements is performed in order to evaluate an agreement between the measurements of the different model-based segmentation measurements. In case of an agreement between the different individual measurements, the accuracy is estimated of the gestational age and all other measurements.

A 3D ultrasound scan typically involves emitting ultrasound waves that illuminate a particular volume within a body, which may be designated as target volume or volumetric region. This can be achieved by emitting ultrasound waves at multiple different angles. A set of volume data is then obtained by receiving and processing reflected waves. The set of volume data is a representation of the target volume within the body over time. Since time is usually denoted as fourth dimension, such ultrasound system 100 delivering a 3D image sequence over time, is sometimes also referred to a 4D ultrasound imaging system.

Figure 5:
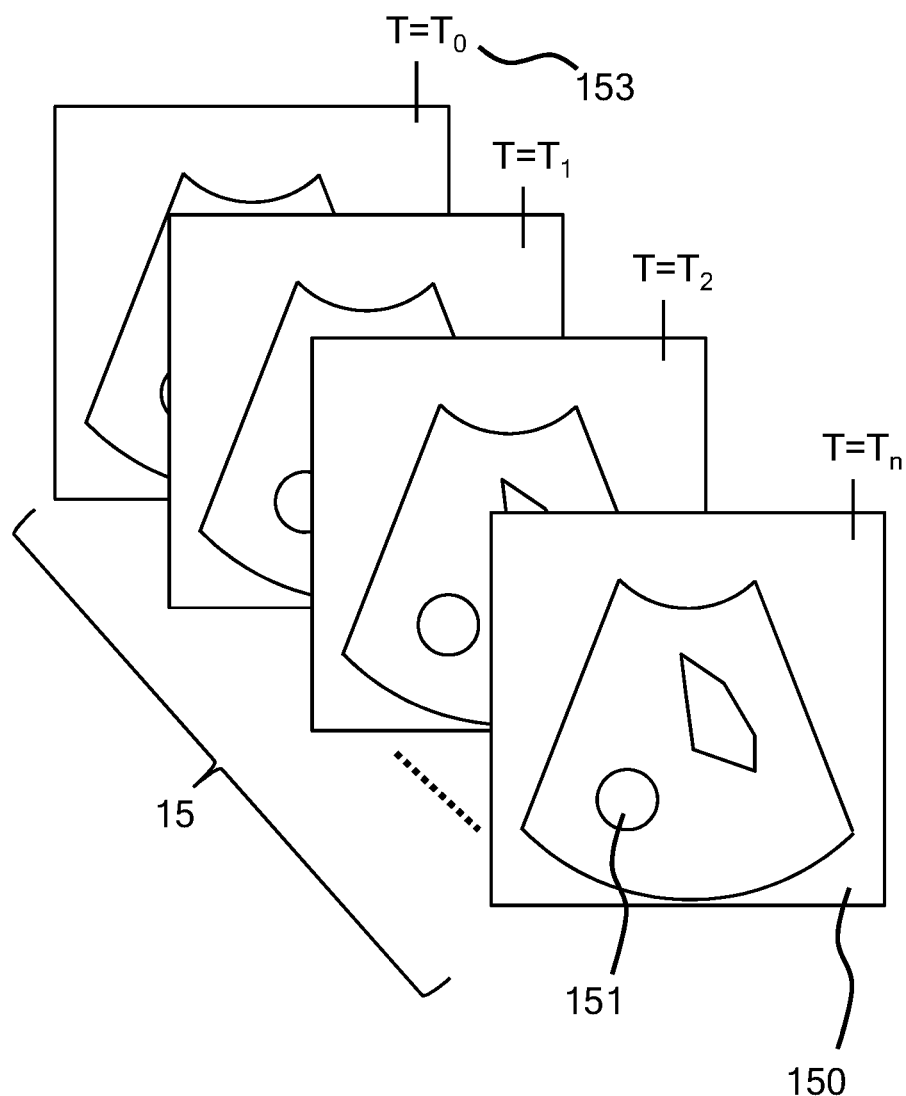
FIG. 5 schematically depicts a sequence of 2-D image frames captured by moving an ultrasound probe across a region of interest of the patient's body.

In contrast, in a 2D ultrasound system 100, such a volumetric region is typically created by the sonographer physically moving the ultrasound probe 14 over an abdominal region of the mother in order to capture a sequence 15 of 2D image frames 150 that may be evaluated by the sonographer to obtain an impression of part of the prenatal entity including an anatomical feature of interest 151, as schematically depicted in FIG. 5. Such an anatomical feature of interest may be any anatomical feature that can be automatically recognized in an image frame 150 by a suitable segmentation algorithm. Such algorithms are well-known per se and are widely available, such that they will not be further explained in the present application for the sake of brevity only. Non-limiting examples of such anatomical features include fetal head, abdomen, bone structure such as femur or spine, and so on. The sonographer may be interested in the evaluation of such anatomical features to determine gestational development, abnormalities, and so on.

Whereas 3D volume data may be re-sliced to give a better viewing angle in case an original viewing angle of the volumetric region did not accurately display or even failed to display the anatomical feature of interest, in 2D imaging the viewing angle is determined by the direction in which the sonographer moves the ultrasound probe 14 over the mother's abdominal region. However, obtaining the optimal direction in which the sonographer is to move the ultrasound probe 14 over the body region of interest (here the mother's abdominal region) is a non-trivial exercise requiring skill and experience. Consequently, upon acquiring the sequence 15 of 2-D image slices 150, subsequent evaluation of this sequence may indicate that the anatomical feature of interest 151 is not consistently visible across the sequence 15, e.g. missing from and/or distorted in at least some of the image slices 151. In such a scenario, the sonographer will need to generate a new sequence 15 of 2-D image slices 150 by moving, i.e. translating, the ultrasound probe 14 over the body region of interest in a different direction, in the hope that this improves the visibility of the anatomical feature of interest 151 in the image slices 150. As can be appreciated, this is a trial and error exercise, which therefore can be rather time-consuming and frustrating for the sonographer as well as traumatic for the patient.

Figure 6:
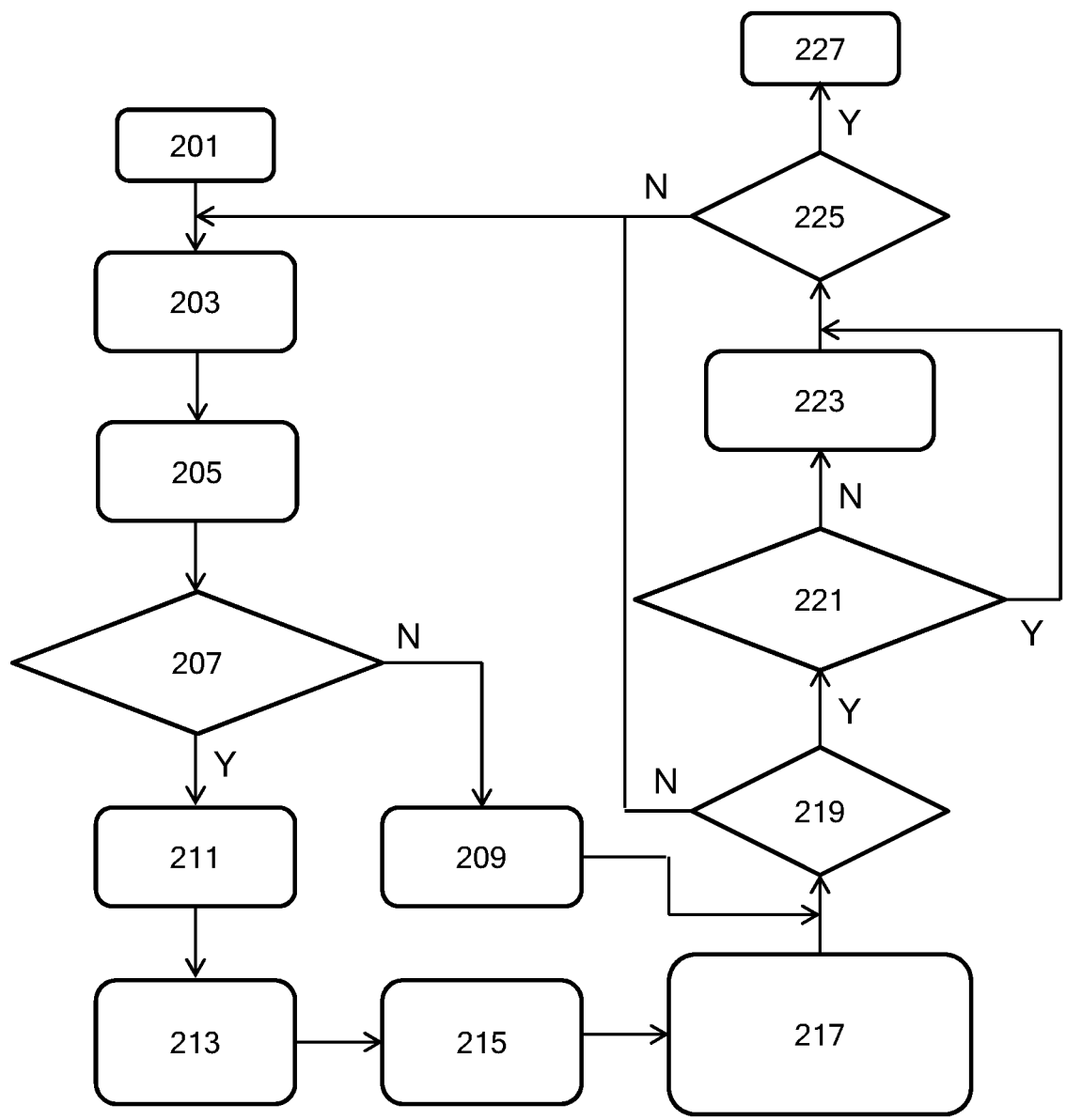
FIG. 6 is a flowchart of a method of operating an ultrasound system according to an embodiment.

Embodiments of the present invention seek to provide real-time visual feedback to a sonographer indicative of the suitability of a sequence 15 of 2-D image slices 150 for the evaluation of such an anatomical feature of interest during acquisition of the sequence such that the sonographer can adjust the direction in which he or she moves the ultrasound probe 14 across the body region of interest of the patient in accordance with this visual feedback. To this end, according to one aspect of the present invention, the processor arrangement of the ultrasound system 100 may be adapted to implement a method 200 of operating the ultrasound system 100 in order to generate such visual feedback, a flowchart of which is shown in FIG. 6, which flowchart depicts an example embodiment of this method 200 although it should be understood that variations to this method, e.g. a variation in the order in which the operations depicted in this flowchart are performed, may be contemplated without departing from the teachings of the present invention.

The processor arrangement may be embodied by a single processor or by a plurality of processors distributed across the ultrasound system as previously explained and may be adapted in any suitable manner to implement the embodiments of the method 200. For example, the desired functionality may be implemented by one or more dedicated hardware components of the ultrasound imaging apparatus 100, or alternatively may be realized in software for execution on a suitably configured processor arrangement, e.g. in the form of computer program instructions such as algorithms that cause such a suitably configured processor arrangement to implement the method 200.

The method 200 starts in operation 201, for example by a sonographer commencing a scan of a patient with the ultrasound probe 14, typically by moving, i.e. translating, the ultrasound probe 14 along a body region of interest of the patient such as an abdominal region of a mother carrying a prenatal entity such as a fetus. In operation 203, the processor arrangement, e.g. the image reconstruction unit 16, receives a 2-D image frame 150, preferably with a timestamp 153, from the ultrasound probe 14 and attempts to segment the received image frame in operation 205 using a suitable segmentation algorithm as previously explained in order to recognize an anatomical feature of interest 151 of the prenatal entity. In an embodiment, the ultrasound system 100 may contain a plurality of such segmentation algorithms for recognizing different anatomical features of interest of such a prenatal entity, in which case the sonographer may select the anatomical feature of interest using the user interface 20, e.g. by selecting the anatomical feature of interest 151 from a selection menu displayed on the display device 18 in operation 201 prior to commencing the capturing of the sequence 15.

In operation 207, it is checked if the attempted segmentation of the received image frame 150 was successful. If not, the image frame 150 may be considered as being incorrect or at least unsuitable for the evaluation of the anatomical feature of interest, which may cause the method 202 proceeds to operation 209 in which the image frame 150 is rejected for further processing. This may further comprise discarding the image frame 150 although alternatively the rejected image frame 150 may be stored in the data storage arrangement 60, e.g. together with a rejection indication such that in a later evaluation mode the rejected image frame may be immediately recognized as rejected.

On the other hand it is determined in operation 207 that the attempted segmentation of the received image frame 150 was successful, the method 200 proceeds to 211 in which a geometric property of the recognized anatomical feature of interest 151 is automatically determined in the segmented image frame 150, e.g. with the segmentation algorithm. Such a geometric property for example may be a dimension of the geometric feature of interest 151, e.g. a diameter or circumference of the fetus head or abdominal region, a femur length, nuchal translucency, bi-parietal diameter, and so on, as will be readily understood by the skilled person. The determined geometric property of the recognized anatomical feature of interest 151 may be stored in the data storage arrangement 60 in operation 213 together with the associated 2-D image slice 150 and its timestamp 153 for subsequent evaluation, e.g. an interactive review operation of the sequence 15 as will be explained in more detail below.

In operation 215, the processor arrangement determines a temporal variance of the geometric property of the anatomical feature of interest 151. To this end, the processor arrangement may maintain a sliding window of image frames 150 in which a fixed number of accepted image frames are kept together with the determined geometric property of the anatomical feature of interest 151 as derived from the segmented image frames 150 kept in the sliding window. For example, the sliding window may be implemented as a buffer of size N, in which N is a positive integer of any suitable size, e.g. of size 10. As will be understood by the skilled person, the choice of the actual value of N is a design choice which may be made based on a trade-off between accuracy of the variance estimation and computational effort required to estimate this variance. The buffer may form part of the data storage arrangement 60 or alternatively may form part of the processor arrangement, e.g. on on-chip memory such as a cache memory or the like.

The temporal variance may be a variation of the dimension of the anatomical feature of interest 151 across the image frames 150 in the sliding window, or alternatively or additionally may be a variation in the positioning of the anatomical feature of interest 151 across the image frames 150, e.g. a change in center of gravity of the anatomical feature of interest, which may be indicative of the acquisition direction of the sequence 15 of image frames 150 being misaligned with a typical propagation direction of the anatomical feature of interest, which may cause the extracted dimensional of the anatomical feature of interest 151 across the image frames 150 to be susceptible to inaccuracy.

The temporal variance in the geometric property of the anatomical feature of interest 151 as derived from the sliding window of image frames 150 is a useful indicator of the stability and therefore the reliability of the sequence 15 of image frames 150 as captured by the sonographer moving the ultrasound probe 14 across the body region of interest of the patient under investigation. Therefore, a visual representation of this temporal variance when displaying captured image frames 150 during the acquisition of the sequence 15 is a useful indicator to the sonographer of whether the direction in which he or she moves the ultrasound probe across the body region of interest of the patient under investigation will lead to a sequence 15 of ultrasound image frames 150 from which the geometric property of the anatomical feature of interest 151 of the prenatal entity can be reliably obtained.

Figure 7:
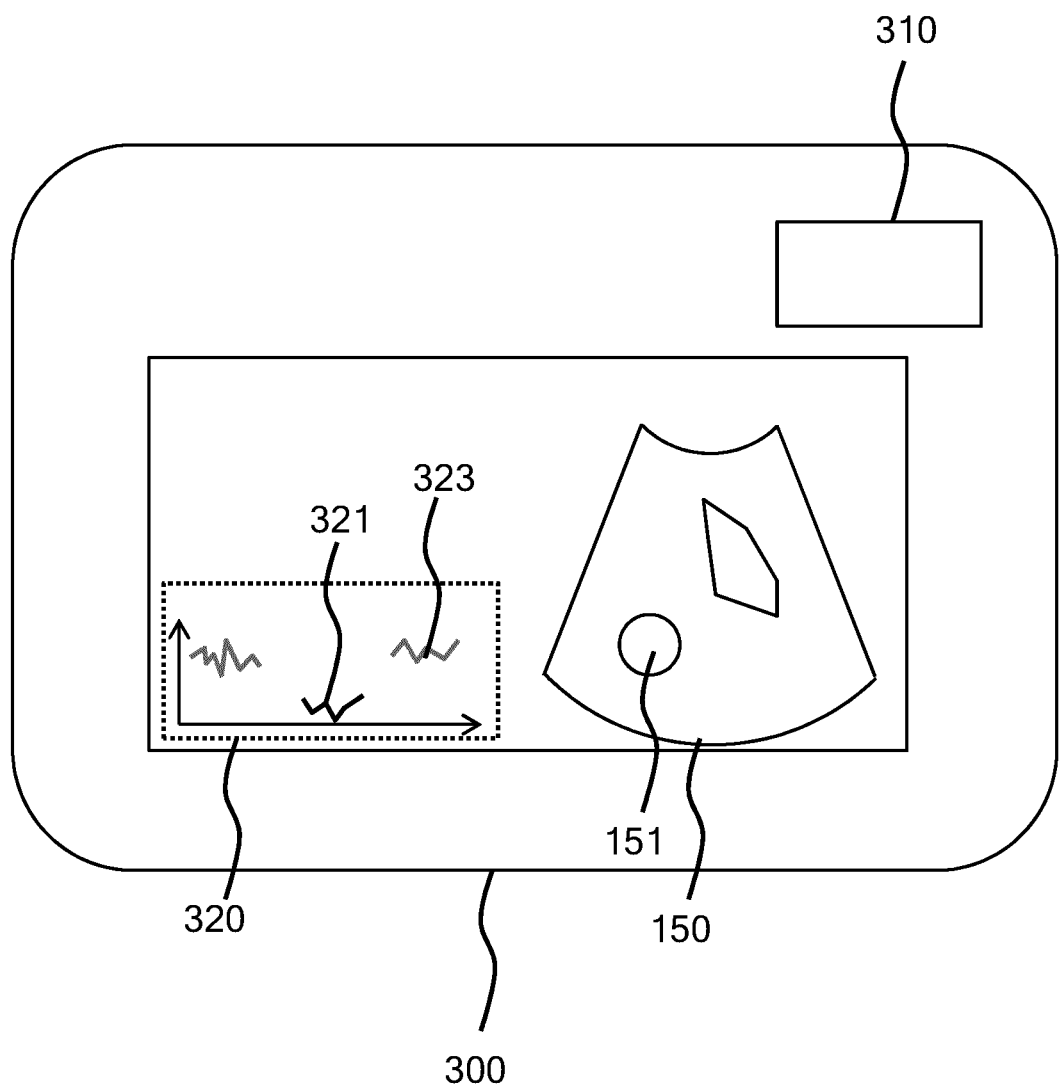
FIG. 7 schematically depicts a view generated on a display device in accordance with a method of operating an ultrasound system according to an embodiment.

To this end, in operation 217, the processor arrangement controls the display device 18 such that together with each displayed image frame 150, the determined geometric properties of the accepted image frames 150 in said sequence 15, e.g. the determined geometric properties of the accepted image frames 150 in the sliding window, are also displayed, typically such that the temporal variance of these geometric properties across the image frames in the sliding window can be readily recognized by a sonographer looking at the display device 18. A non-limiting example of such a displayed image 300 as displayed on the display device 18 is schematically depicted in FIG. 7, which image 300 includes the 2-D image frame 150, e.g. an accepted 2-D image frame in which the anatomical feature of interest 151 can be recognized by a segmentation algorithm as previously explained, together with the history 320 of geometric properties derived from previously received accepted image frames 150, e.g. a fixed number of previously received image frames stored in a fixed size buffer implementing a sliding window of such frames as previously explained. Such a history 320 for example may be displayed as a graph or diagram from which a sonographer can immediately derive the variation across the historically obtained geometric properties.

In an embodiment, the processor arrangement is further adapted to compare each determined geometric property against a reference value such as an expectation value of the geometric property based on the normal development of the prenatal entity at a certain development stage and to control the display device 18 to display each determined geometric property in a manner indicative of a result of this comparison. For example, in the history 320, historic geometric properties 321 falling within a tolerance range of such a reference value may be displayed in a manner different to geometric properties 323 falling outside this tolerance range such that the sonographer can immediately assess whether or not most historic geometric properties can be considered reliable. For example, reliable geometric properties 321 may be given a first colour, such as green, whereas unreliable geometric properties 323 may be given a second colour different to the first colour, such as red. Of course, many other distinguishing visualizations of the geometric properties 321 and 323 will be immediately apparent to the skilled person. The tolerance range may also be displayed, e.g. as a confidence interval with upper and lower bounds around each displayed geometric property to further assist the sonographer in assessing the reliability of the respective geometric properties represented by the history 320.

In an embodiment, the processor arrangement is further adapted to control the display device 18 to display the determined geometric property of the recognized anatomical feature of interest 151 in an accepted image frame 150 together with this image frame such that the sonographer is provided with a real-time indication of the geometric property of this anatomical feature during acquisition of the sequence 15. This may further aid the sonographer the assessment of the prenatal entity under investigation. The determined geometric property may be displayed in any suitable manner, for example as an overlay 310 of the associated image frame 150 displayed on the display device 18. Such an overlay may be colour-coded based on the comparison of the geometric property against the reference value as previously explained, such that a reliable geometric property, e.g. a reliable dimension such as a circumference or diameter, may be readily distinguishable from an unreliable geometric property. For example, a reliable geometric property may be shown in green whereas an unreliable geometric property may be shown in red although other colours of course may be chosen. Preferably, the same colour coding scheme as used for the history 320 to distinguish between reliable and unreliable values of the geometric property is also used for the overlay 310.

At this point it is noted that an image frame 150 rejected in operation 209 may also be displayed on the display device 18 together with a warning that the image frame 151 is rejected at least for the purpose of biometric measurement acquisition. Such a warning may be any suitable visible warning, such as a flashing or constantly coloured region on the screen of the display device 18, an audible warning, and so on.

The method 200 may further evaluate if a sequence 15 of image frames 150 as received from the ultrasound probe 14 is sufficiently stable in terms of variance of the geometric property of the anatomical feature of interest 151 such that a sonographer can decide whether the sequence 15 can be relied upon or whether the sequence 15 needs to be recaptured. To this end, the method 200 may check in operation 219 if the acquisition of the sequence 15 has been completed. This for example may be determined based on a user command received from the ultrasound probe 14 or the user interface 20 indicative of this completion or based on the sliding window, e.g. the data storage buffer, being full. Other ways of determining whether the sonographer has completed acquisition of a sequence 15 will be apparent to the skilled person.

If it is determined in operation 219 that acquisition of the sequence 15 of image frames 150 is not yet complete, the method 200 reverts back to operation 203 in which the next image frame 150 of the sequence 15 is received. On the other hand, if it is determined in operation 219 that acquisition of the sequence 15 is complete, the method 200 proceeds to operation 221 in which at least the stability and preferably the stability as well as the availability of the anatomical feature of interest 151 in the image frames 150 of the sequence 15 is evaluated. For example, the processor arrangement may determine a variation in the determined geometric property across the plurality of image frames 150 of the sequence 15 accepted in operation 207. Such a variation may involve determining an average value of the geometric property across the plurality of image frames 150 and checking that each image frame 150 is associated with a determined geometric property that lies within a certain tolerance range of this average value. Alternatively, this may involve comparing each of the geometric properties against the aforementioned reference value. Other suitable metrics will be apparent to the skilled person. In this manner, it can be determined if the sequence 15 is stable or noisy.

In an embodiment, this determination may be based on a combination of the determination of this variance and the ratio of the total number of accepted image frames 150 in the sequence 15 and the total number of image frames 150 in the sequence 15, i.e. including the image frames 150 rejected in operation 207. If this ratio falls below a defined threshold, this may be a further indication that the sequence 15 is noisy, such that the sequence 15 may be considered unreliable if at least one of the variance of the geometric property across the sequence 15 is too high and the acceptance rate of image frames 150 in operation 207 is too low.

The processor arrangement may control the display device 18 to display the evaluation result obtained in operation 221, e.g. by a red light in case of a noisy sequence 15 and by a green light in case of a stable sequence 15. Other distinguishable ways of highlighting the different outcomes of this evaluation will be immediately apparent to the skilled person and may be equally contemplated within the context of the teachings of the present application.

If the sequence 15 of image frames 150 is considered to be noisy in operation 221, the method 200 may proceed to operation 223 in which the sequence 15 is rejected. Such rejection may be automatic and may cause the removal of the image frames 150 and associated data such as the geometric property of the anatomical feature of interest 151 in the image frames 150 from the data storage arrangement 60. Alternatively, the sonographer may be prompted, e.g. by a displayed message on the display device 18, to confirm that the sequence 15 can be removed from the data storage arrangement 60. In the latter scenario, the sonographer may decide to keep sequence 15 despite the sequence being considered noisy, in which case operation 223 may not include deletion of the accepted image frames 150 of the sequence 15 from the data storage arrangement 60. On the other hand, if the sequence 15 of image frames 150 is considered to be stable enough in operation 221, the method 200 may proceed directly to operation 225 in which it is determined if the sonographer wish to acquire another sequence 15 of image frames 150. This determination may be made in any suitable manner, for example by responding to a user instruction provided via the ultrasound probe 14 or the user interface 20 indicative of the wish to acquire such a further sequence 15. If this is the case, the method 200 may revert back to operation 203; otherwise, acquisition of the image frames 150 may terminate in 227, e.g. the method 200 may enter an interactive review mode as will be explained in more detail below.

In this manner, a sonographer is provided with real-time feedback regarding the reliability and suitability of the sequence 15 of image frames 150 captured by the sonographer such that a sonographer is provided with real-time guidance concerning the acquisition of the image frames 150, which guidance for example may assist the sonographer in guiding the ultrasound probe 14 in an appropriate direction across the body region of interest of the patient as explained in more detail above.

However, it should be understood that embodiments of the present invention are not limited to the provision of real-time feedback to a sonographer. In an embodiment, the data collected with the method 200 as described above may be used in an interactive review mode of the ultrasound system 100 in which a sonographer may use the user interface 20 to browse through the history of image frames 150 stored in the data storage arrangement 60 in order to evaluate the recorded image frames 150 and associated segmentation information such as the estimated geometric property of the anatomical feature of interest 151 recognized by the segmentation algorithm in the image frame 150. To facilitate navigation, the processor arrangement for example may cause the display device 18 to display a timeline derived from the timestamps 153 recorded for each stored image frame 150, such that the sonographer may scroll along the displayed timeline in order to retrieve an image frame 150 corresponding to a particular timestamp from the data storage arrangement 60 and display the retrieved image frame 150 on the display device 18. This may further include the display of the determined geometric property of the recognized anatomical feature of interest 151 as recognized by the segmentation algorithm in this image frame 150, which geometric property may be displayed in any suitable manner, such as for example as an overlay as explained in more detail above. Similarly, the segmentation of the image frame 150 may be displayed as an overlay or in any suitable alternative manner as will be immediately apparent to the skilled person.

Navigation along such a timeline has the further advantage that the sonographer may identify an image frame 150 in which the anatomical feature of interest 151 is particularly well represented, e.g. clearly visible without distortions. Based on the timestamp 153 associated with such an identified image frame 150, the sonographer may be able to estimate the position of the ultrasound probe 14 on the body region of interest in which this image frame was captured, such that the knowledge of this position may be used by the sonographer to obtain a further sequence 15 if desired to obtain a further improved clarity or visibility of the anatomical feature of interest 151 in this further sequence.

In an embodiment, the processor arrangement may calculate an average geometric property for a subset of the stored image frames 150 and cause the display device 18 to display this average geometric property. Such a subset for example may be compiled in response to the selection of a particular image frame 150 by the sonographer, which subset contains a number of image frames 150 neighbouring the selected image frame, such that a sonographer is presented with an average value of the geometric property of interest, e.g. a dimension of the anatomical feature of interest 151, which may aid the sonographer in evaluating this anatomical feature, as it is for instance obviated the need for the sonographer to evaluate a series of individual image frames 150 to obtain this geometric property for a volumetric region of the prenatal entity, e.g. a fetus.

The sonographer may further use this interactive review mode to manually correct determined geometric properties of the anatomical feature of interest 151 and/or manually correct proposed segmentations of the stored image frames 150 in order to improve the accuracy of the evaluation of this geometric property if necessary. Where the sonographer manually corrects a proposed segmentation of a stored image frame 150, the processor arrangement may automatically recalculate the geometric property of the corrected segmentation of the anatomical feature of interest 151. The processor arrangement may further be adapted to automatically update the data storage arrangement 60 with the corrections made based on the input of the sonographer.

At this point, it is noted that embodiments of the present invention have been described in terms of acquisition of 2-D image frames 150 by a sonographer manually moving an ultrasound probe 14 across a body region of interest in a translation direction of the ultrasound probe 14 to define a sliding window of 2-D image frames 150, each imaging a different slice of the fetus 62. However, it should be understood that the principles of the present invention equally may be applied to 3-D ultrasound images in which the sonographer may not have to move the ultrasound probe 14 across a body region of interest but in which the sonographer may need to decide in which direction to slice the volumetric image in order to obtain 2-D image slices corresponding to the 2-D image frames 150 for further evaluation, e.g. to determine the geometric property of the anatomical feature of interest 151. In this case, the method 200 may evaluate each of the 2-D image slices in order to determine the stability (variability) of the sequence of image slices as explained in more detail above such that a sonographer is provided with real-time feedback about the suitability of the chosen slicing direction such that a sonographer can obtain guidance as to in which direction the volumetric image should be sliced, in which case the slice direction defines the translation direction in which the sliding window of image slices is generated, in order to reliably obtain this geometric property.

The above described embodiments of the method 200 may be realized by computer readable program instructions embodied on a computer readable storage medium having, when executed on a processor arrangement of the ultrasound system 100, cause the processor arrangement to implement the method 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, an ultrasound imaging apparatus is adapted to retrieve the computer readable program instructions from such a computer readable storage medium and to create a new computer readable storage medium by storing the retrieved computer readable program instructions in a data storage arrangement, e.g. in a memory device or the like forming part of the data storage arrangement, which data storage arrangement is accessible to the processor arrangement such that the processor arrangement can retrieve the computer-readable program instructions from the data storage arrangement for execution.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound system comprising a processor arrangement and a display device under control of the processor arrangement, wherein the processor arrangement is adapted to:
   receive a sequence of 2-D ultrasound image frames of a prenatal entity from an ultrasound probe, said sequence defining a sliding window of 2-D ultrasound image frames along a translation direction across said prenatal entity, and, for each image frame in said sequence:
   control the display device to display the received image frame;
   attempt to segment the image frame for recognition of an anatomical feature of interest of said prenatal entity in said image frame; and
   accept the image frame for further processing upon recognition of said feature, said further processing comprising:
   determine a geometric property of the recognized anatomical feature of interest for each accepted image frame;
   calculate a deviation of the determined geometric property from a reference value; and
   control the display device to display the determined geometric properties of the accepted image frames in said sequence with each displayed image frame wherein determination of the geometric property comprises determination of a dimension of the recognized anatomical feature and in a manner indicative of a result of said calculation.

2. The ultrasound system of claim 1, wherein the processor arrangement is adapted to control the display device to display the determined geometric properties of the accepted images in said sequence as a graph.

3. The ultrasound system of claim 1, wherein the processor arrangement is adapted to control the display device to display an overlay including the determined geometric property over the recognized anatomical feature of interest of a displayed accepted image frame.

4. The ultrasound system of claim 1, wherein the processor arrangement is adapted to:

determine a variation in the determined geometric property between the plurality of accepted image frames;

reject the plurality of accepted image frames if the determined variation exceeds a defined threshold; and control the display device to display an indication of said rejection.

5. The ultrasound system of claim 4, wherein the processor arrangement is adapted to reject the plurality of accepted image frames if:

the determined variation exceeds the defined threshold; and a ratio of a total number of accepted image frames in a complete sequence of image frames and a total number of image frames in the complete sequence of image frames is below a defined further threshold.

6. The ultrasound system of claim 1, further comprising a data storage arrangement, wherein the processor arrangement is adapted to store the accepted image frames and the determined geometric properties in the data storage arrangement for evaluation of the image frames and/or the determined geometric properties at a later point in time.

7. The ultrasound system of claim 1, further comprising the ultrasound probe.

8. The ultrasound system of claim 1, wherein the sequence of image frames forms part of a volumetric image.

9. A method for operating an ultrasound system comprising a processor arrangement and a display device under control of the processor arrangement, wherein the method comprising, with the processor arrangement:

receiving a sequence of 2-D ultrasound image frames of a prenatal entity from an ultrasound probe, said sequence defining a sliding window of 2-D ultrasound image frames along a translation direction across said prenatal entity, and for each image frame in said sequence:

controlling the display device to display the received image frame;

attempting to segment the image frame for recognition of an anatomical feature of interest of said prenatal entity in said image frame; and accepting the image frame for further processing upon recognition of said feature, said further processing comprising:

determining a geometric property of the recognized anatomical feature of interest for each accepted image frame;

calculating a deviation of the determined geometric property from a reference value; and controlling the display device to display the determined geometric properties of the accepted images in said sequence with each displayed image frame, wherein determination of the geometric property comprises determination of a dimension of the recognized anatomical feature and in a manner indicative of a result of said calculating step.

10. The method of claim 9, further comprising controlling the display device to display an overlay including the determined geometric property over the recognized anatomical feature of interest of an accepted image frame.

11. The method of claim 9, further comprising:

determining a variation in the determined geometric property between the plurality of accepted image frames;

rejecting the plurality of accepted image frames if the determined variation exceeds a defined threshold; and controlling the display device to display an indication of said rejection.

* * * * *